United States Patent
Greenan

(10) Patent No.: US 7,481,836 B2
(45) Date of Patent: Jan. 27, 2009

(54) PROSTHESIS WITH COUPLING ZONE AND METHODS

(75) Inventor: Trevor Greenan, Santa Rosa, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 383 days.

(21) Appl. No.: 11/278,044

(22) Filed: Mar. 30, 2006

(65) Prior Publication Data

US 2007/0233227 A1   Oct. 4, 2007

(51) Int. Cl.
*A61F 2/06* (2006.01)

(52) U.S. Cl. ............... 623/1.23; 623/1.35; 623/1.53

(58) Field of Classification Search ......... 623/1.3–1.34, 623/1.11–1.15
See application file for complete search history.

(56) References Cited

U.S. PATENT DOCUMENTS

| | | | |
|---|---|---|---|
| 4,641,653 A | | 2/1987 | Rockey |
| 4,763,653 A | | 8/1988 | Rockey |
| 5,476,506 A | * | 12/1995 | Lunn ................... 623/1.28 |
| 5,697,970 A | * | 12/1997 | Schmitt et al. .......... 623/1.51 |
| 5,769,882 A | | 6/1998 | Fogarty et al. |
| 6,027,510 A | * | 2/2000 | Alt .................. 606/108 |
| 6,165,214 A | | 12/2000 | Lazarus |
| 6,306,164 B1 | | 10/2001 | Kujawski |
| 6,319,276 B1 | | 11/2001 | Holman et al. |
| 6,395,019 B2 | | 5/2002 | Chobotov |
| 6,602,280 B2 | | 8/2003 | Chobotov |
| 6,733,521 B2 | | 5/2004 | Chobotov et al. |
| 6,761,733 B2 | | 7/2004 | Chobotov et al. |
| 6,776,604 B1 | | 8/2004 | Chobotov et al. |
| 2003/0036745 A1 | | 2/2003 | Khosravi et al. |
| 2003/0074055 A1 | | 4/2003 | Haverkost |
| 2004/0093063 A1 | | 5/2004 | Wright et al. |
| 2004/0243154 A1 | | 12/2004 | Berg et al. |
| 2007/0198079 A1 | * | 8/2007 | Casey et al. ............... 623/1.13 |

FOREIGN PATENT DOCUMENTS

| | | |
|---|---|---|
| JP | WO96/29955 | 10/1996 |
| WO | WO 03/053288 | 7/2003 |

* cited by examiner

*Primary Examiner*—Suzette J Gherbi
(74) *Attorney, Agent, or Firm*—Harry Macey

(57) ABSTRACT

A tubular prosthesis comprises a tubular member having raised portions, which can be formed from and be part of the tubular member. The raised portions form a chamber or discrete space in a body passageway or lumen between the prosthesis and a portion of the passageway or lumen wall in which it is placed. A substance is delivered to the chamber to assist the prosthesis placement. The substance can comprise one or more substances that can enhance the seal and/or fixation characteristics between the prosthesis the passageway wall and/or provide therapeutic benefit. In another embodiment, the raised portions can be collars secured to the tubular member and in yet a further embodiment the raised portions can comprise inflatable collars.

40 Claims, 12 Drawing Sheets

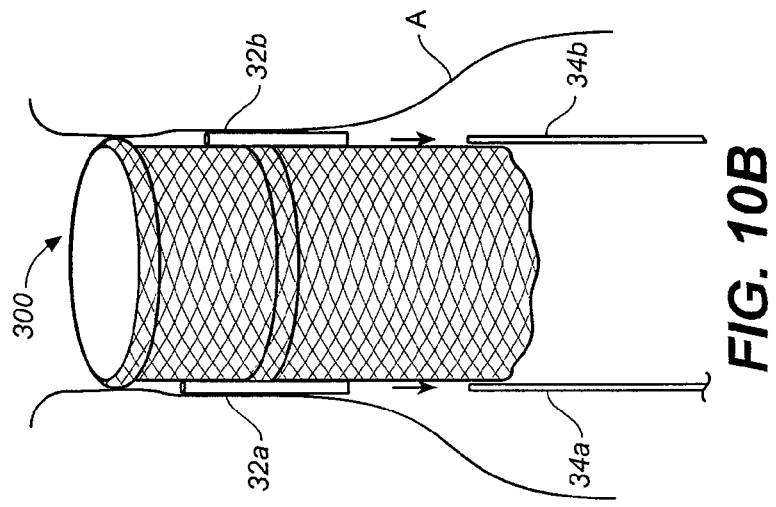
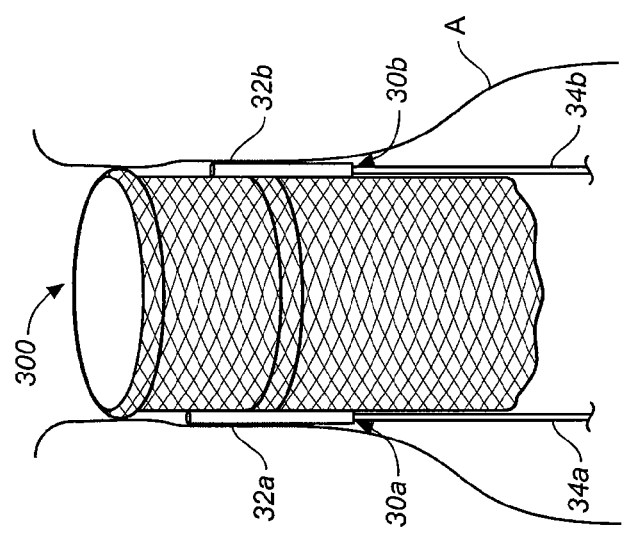
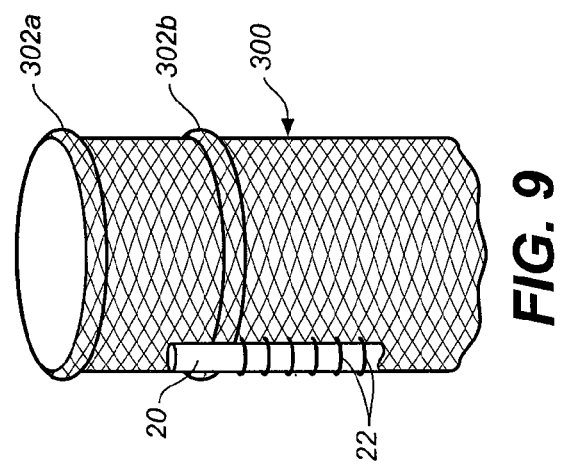

PROSTHESIS WITH COUPLING ZONE AND METHODS

FIELD OF THE INVENTION

The present invention relates to methods and apparatus for the endoluminal placement of devices, such as tubular prosthesis, which can comprise, for example, grafts or stent-grafts.

BACKGROUND OF THE INVENTION

Tubular prostheses including tubular stents, grafts, and stent-grafts (e.g., stents having an inner and/or outer covering comprising a layer of graft material and which may be referred to as covered stents) have been used to treat vascular disorders such as stenoses and aneurysms.

A stenosis involves the narrowing of a duct or canal such as a blood vessel where it generally impedes blood flow. Stenoses have been treated using self-expanding or balloon expandable tubular prostheses (e.g., a balloon expandable device), which are positioned within the stenotic portion of a blood vessel, for example, to maintain lumen integrity after the vessel has been widened or to widen the vessel to improve or restore desirable blood flow therethrough.

In contrast, an aneurysm involves abnormal widening of a duct or canal such as a blood vessel and generally appears in the form of a sac formed by the abnormal dilation of the duct or vessel wall. The abnormally dilated wall typically is weakened and susceptible to rupture. Aneurysms can occur in any blood vessel including the abdominal aorta. Rupture of an abdominal aortic aneurysm, which is below the renal arteries and extends distally to or toward the iliac arteries, can be fatal. Tubular prostheses including grafts and stent-grafts have been used to treat aneurysms. They are generally placed to extend through the aneurysmal sac and beyond the proximal and distal ends thereof to replace or bypass the dilated wall. When used in blood vessels, the tubular wall of the prosthesis is designed to prevent blood flow therethrough so that the blood bypasses aneurysmal sac. The prostheses described above can be implanted in an open surgical procedure (grafts) or placed endovascularly (stent grafts).

In open vascular surgery, the space around the diseased vessel is surgically opened, the vessel is opened, and the graft ends are sutured into position inside of or as a substitute for the diseased vessel. In contrast, the endovascular or minimally invasive approach typically involves providing a delivery catheter loaded with a radially compressed or folded prosthesis, delivering the catheter and prosthesis into the vasculature (e.g., into a femoral artery), and delivering the prosthesis endovascularly to the aneurysm location. The prosthesis is deployed at the target site where it is either expanded through the use of a balloon or a radial restraint is removed to allow the device to radially expand if it is a self-expanding device. For example, if the prosthesis is a self-expanding stent graft, the stent graft radially expands from its compressed configuration to its expanded configuration upon release of a restraint (e.g., a sheath or the inner wall of the delivery catheter) that maintains the stent graft in its low profile compressed configuration for delivery through the vasculature.

Although the endoluminal approach is much less invasive, and usually requires less recovery time and involves less risk of complication as compared to open surgery, methods of improving fixation and reducing migration continue to be of interest. The outward spring force of a self-expanding stent-graft if not sized and positioned with an adequate interface pressure may not be sufficient to prevent migration. This problem can be exacerbated when the vessel's fixation zone is not round or is calcified. Migration can result in leakage of blood around the prosthesis and into the aneurysmal sac, which, in turn, may increase the chance of rupture of the dilated vessel wall. When there is a short landing zone between the aortic aneurysm and a proximal branching artery (e.g., the renal arteries, carotid or brachiocephalic artery) small deviations in sizing and placement may result in migration and/or leakage.

Radially extending members such as tines, barbs, hooks and the like that engage the vessel wall, are used in some devices to minimize migration.

One method has been to simply inject a filler substance, such as foam, into the aneurysmal sac after the stent-graft has been placed in the desired location Other approaches using such substances have been to incorporate a substance onto a stent-graft such as cat gut cellulose and nylon, see U.S. Pat. No. 6,165,214. These approaches, however, have limitations. The incorporation of the substance into the stent-graft approach is limited in the amount of the substance that can be incorporated into the device and then delivered. And an approach where a substance is simply injected at the proximal neck does not provide for containment of the substance. As a result, the substance can flow away from the neck, thereby reducing its effectiveness.

There remains a need to develop and/or improve seal and/or fixation approaches for endoluminal or endovascular prostheses placement.

SUMMARY OF THE INVENTION

The present invention involves improvements in prosthesis placement and overcomes disadvantages of prior art.

In one embodiment according to the invention, a tubular prosthesis comprises a tubular member adapted for placement in a lumen in a human body. The tubular member has first and second ends and first and second raised portions that are separate from one another and are adjacent to one of the ends, each raised portion extends in a circumferential direction about said tubular member and is integrally formed in the tubular member. Among the many advantages of the invention is that one can, in a controlled manner, deliver between the raised portions, material comprising one or more substances that can enhance the seal and/or fixation characteristics between the prosthesis and the lumen and/or provide therapeutic benefit.

In another embodiment according to the invention, a tubular prosthesis comprises a tubular member adapted for placement in a lumen in a human body. The tubular member has first and second end portions and first and second raised portions adjacent to one of said end portions, each raised portion is annular and integrally formed in the tubular member and the tubular member comprises braided material.

In another embodiment according to the invention, a tubular prosthesis system comprises a tubular member, which is adapted for placement in a passageway having a wall and being in a human body, and a delivery tube. The tubular member has first and second end portions, first and second separate raised portions, each extending in a circumferential direction about said tubular member, and an intermediate portion between the raised portions, which together with the raised portions forms a 360° annular channel. The raised portions are exposed so that the raised portions can directly engage the wall to form a chamber into which a substance can be delivered when the tubular prosthesis is positioned at a target location in the passageway. The delivery tube is secured to the tubular member and has an inlet and an outlet, the outlet being disposed between the raised portions and arranged to deliver a substance therebetween.

In another embodiment according to the invention, a method of delivering a substance between a prosthesis and a passageway wall in a human body comprises positioning a tubular endoluminal prosthesis, having an annular channel formed along a circumferential exterior surface thereof, in a passageway, having a wall and being in a human body, so as to form a discrete chamber with the channel and a portion of the wall, and introducing a substance into said chamber.

The above is a brief description of some features in the prior art and advantages of the present invention. Other features, advantages, and embodiments accordingly to the invention will be apparent to those skilled in the art from the following description and accompanying drawings.

BRIEF DESCRIPTION OF THE DRAWINGS

FIG. 5 depicts an abdominal aortic aneurysm to be treated and a contrast delivery catheter positioned with its outlet end in the vicinity of the renal arteries; FIG. 6 depicts the endoluminal device positioned to bypass the aneurysm; FIG. 7 depicts introducing a substance into the chamber that the device forms with the aorta after the contrast delivery catheter has been partially withdrawn so as to have its discharge end disposed in the chamber between the illustrative proximal neck raised portions of the endoluminal device, together with an optional fluid discharge or evacuation tube or catheter that facilitates fluid (e.g., blood) discharge or evacuation from the chamber; FIG. 8 illustrates the endoluminal device of FIG. 3 with the contrast delivery and fluid evacuation tubes or catheters fully withdrawn after the desired substance was delivered into the proximal neck chamber and the chamber between the ipsilateral leg raised portions and another substance delivery tube (50) being withdrawn after delivering substance to the chamber between the contralateral leg raised portions.

FIG. 9 illustrates another embodiment where the substance delivery tube or lumen is releasably attached to the endoluminal device depicted in FIG. 3.

FIGS. 10A and 10B illustrate another embodiment where the substance delivery tube or lumen comprises a plurality of portions where at least one portion is releasably coupled to the endoluminal device where FIG. 10A shows the portions coupled and FIG. 10B shows one portion withdrawn from the other.

DETAILED DESCRIPTION

The following description will be made with reference to the drawings where when referring to the various figures, it should be understood that like numerals or characters indicate like elements.

A device and method according to the invention involves forming a chamber or discrete space in a body passageway or lumen for receipt of a substance between a prosthesis placed therein and a portion of the passageway or lumen wall and/or apparatus therefor. The substance can comprise one or more substances that can enhance the seal and/or fixation characteristics between the prosthesis and the passageway wall and/or provide therapeutic benefit. These substances can be referred to as active substances.

According to one embodiment, a tubular prosthesis is transluminally delivered to and implanted at a target location within a body lumen or passageway. The prosthesis has a channel, which with the inner wall of the lumen or passageway, forms a discrete space or chamber for receipt of a substance. The tubular prosthesis can be in the form of a stent-graft or the like and can be configured for placement in a variety of body lumens or passageways including, but not limited to, blood vessels (where it can provide an area of at least partial hemostasis or an area at least partially protected from blood flow). Exemplary uses include, but are not limited to, the treatment of vascular diseases such as aneurysms. For example, the tubular prosthesis is especially useful in the endovascular treatment of abdominal aortic aneurysms.

Figure 1:
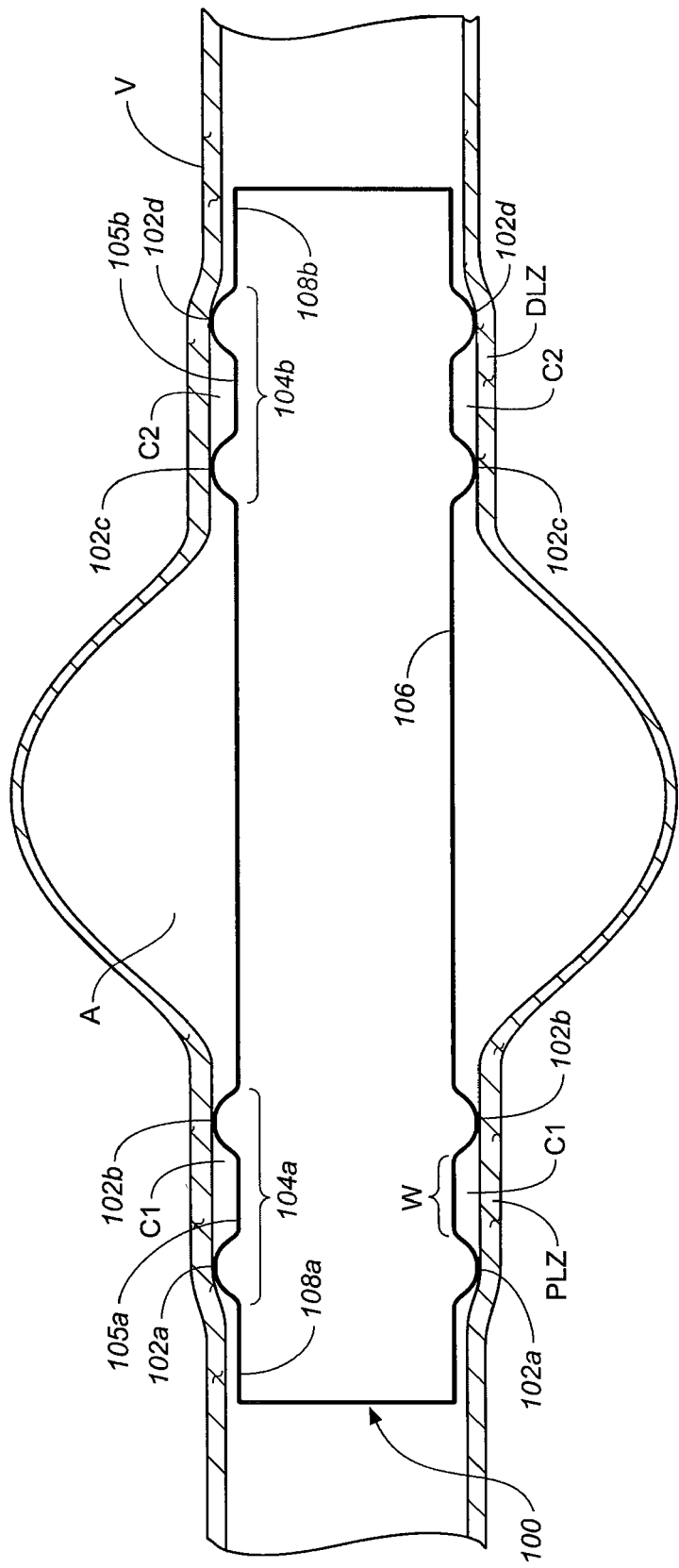
FIG. 1 diagrammatically illustrates a deployed endoluminal device in accordance with the invention.

Referring to FIG. 1, one exemplary prosthesis embodiment is diagrammatically illustrated and generally designated with reference numeral 100. Tubular prosthesis 100 is shown deployed within vessel "V" so as to bypass aneurysm "A." It extends along the aneurysm's proximal landing zone PLZ, bypasses the aneurysmal sac, and extends along the aneurysm's distal landing zone DLZ. In the illustrative embodiment, endovascular prosthesis 100 includes annular raised portions 102a, b, c, d, sealing and/or fixation portions 104a, b, central portion 106 between raised portion pairs, and end portions 108a, b.

Raised portions 102a, b, c, d, are separate and axially spaced from one another and may be referred to as rings. Each portion 105a and 105b of the prosthesis between one of the illustrative ring pairs 102a, b and 102c, d, forms with the ring pair an annular 360° channel. Each channel forms with the inner wall of the vessel or endoluminal wall an annular 360° chamber indicated with reference characters "C1" and "C2," respectively. Substances can then be remotely introduced through a catheter in sufficient quantities and contained within either or both of the chambers depending on the application. The substance can be selected to enhance the ability to seal and/or fix the prosthesis to the vessel wall and/or provide therapeutic benefit to the region or vessel as will be described in more detail below.

Figure 11A:
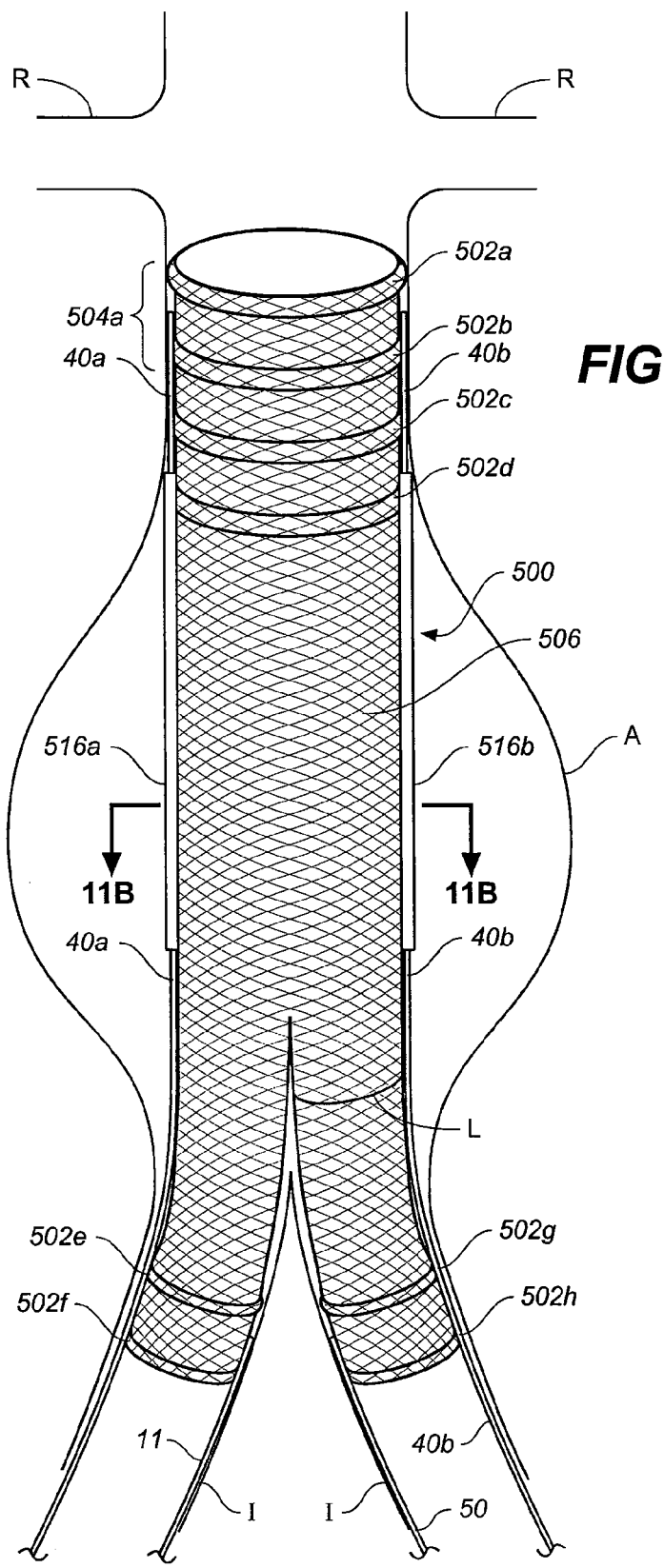
FIG. 11A depicts a further embodiment where a tubular member is permanently secured to or integrally formed with the endoluminal device to support and guide a substance delivery tube or lumen.

The size and position of raised portions 102 depend on the application. The following dimensions apply to all of the embodiments described herein. Generally, the channel width "W" or space between a raised portion pair (measured at the raised portion bases adjacent to portions 105a, b or juncture of the raised portions with portions 105a, b) will be about 5-30 mm. However, when using a multiple channel embodiment as shown in FIG. 11A, which will be described in more detail below, the distance between adjacent raised portions along a particular neck (e.g., between 502a and 502b; 502b and 502c; 502c and 502d; 502e and 503f; or 502g and 502h) will be about 2-10 mm. Thus, the channel width "W" can be about 2-30 mm. Each raised portion extends about 1-5 mm radially outward from the base of the raised portion and has a base width of about 2 mm. It also should be understood that raised portions 102a, b, c, d, or any of the raised portions described herein can be provided at both ends as depicted, for example, in FIG. 1 or only one end. Typically, they are more likely to be provided at both ends in thoracic applications. However, when a bifurcated variation is used for an abdominal aortic aneurysm, the raised portions may only be required at the proximal end of the prosthesis, which is the end that is oriented towards the oncoming flow of blood and the end that is to engage the proximal neck of the aneurysm. This may be the case if below the bifurcation, the iliac arteries are in a condition that conventional mechanical devices can provide an acceptable connection.

Various methods can be used to deliver the substance into the chamber or space formed between the prosthesis channel and endoluminal wall. According to one example, a contrast delivery catheter is used to assist in imaging the target location during prosthesis delivery. Once the prosthesis is deployed at the target location, the catheter is withdrawn so that its outlet port is positioned between the raised portions or between the proximal channel and endoluminal wall of the passageway, and the substance injected into proximal (or first) chamber "C1." In one embodiment, the contrast delivery catheter is further withdrawn so that its outlet port is disposed in the chamber "C2" formed at the other end of the prosthesis to fill that chamber. To facilitate locating the raised portions when moving the contrast delivery catheter, radiopaque markers can be provided along or in the vicinity of the raised portions. As an alternative to the contrast delivery catheter, an injection tube or lumen can be releasably coupled to the prosthesis or stent-graft by breakable sutures or adhesives prior to delivery so that its outlet port is positioned between the raised portions. These tubes can be either separately withdrawn after the procedure or fixed to the catheter center member that is removed after the procedure.

The substance, which may be referred to as an active substance, can comprise any one or combination of any of the following: tissue adhesives to secure the prosthesis to the endoluminal wall and provide a seal therebetween (e.g., cyanoacrylates, fibrin based tissue adhesives (which may or may not include growth factor), and the like); growth factor for enhancing connective cell growth between the tissue wall and the prosthesis; a thrombus promoting agent such as thrombin; and/or a therapeutic drug such as Doxycycline to stabilize the neck of an aneurysm by preventing or minimizing further progression of the aneurysm thereto.

The mechanical and/or chemical properties of the raised portions of the prosthesis and the section of the prosthesis between the raised portions can be modified to improve interaction with a specific substance. For example, the prosthesis can include graft material that is more porous to improve bonding with an adhesive. Further, other known anchoring mechanisms can be used in addition to the active substances described above. Such mechanisms include undulating bare spring wires 414a and 414b provided at the ends of the prosthesis as shown in FIG. 4. The undulating wire is biased radially outward to provide a radial outward spring force when positioned within a vessel or passageway. Hooks, tines and/or barbs also can be incorporated into end portions of the prosthesis as is known in the art. The overall prosthesis configuration also can vary depending on the application. It can have a simple tubular configuration, bifurcated configuration, or other configuration suitable for placement in the target area of a human passageway so that it conforms therewith.

Figure 2:
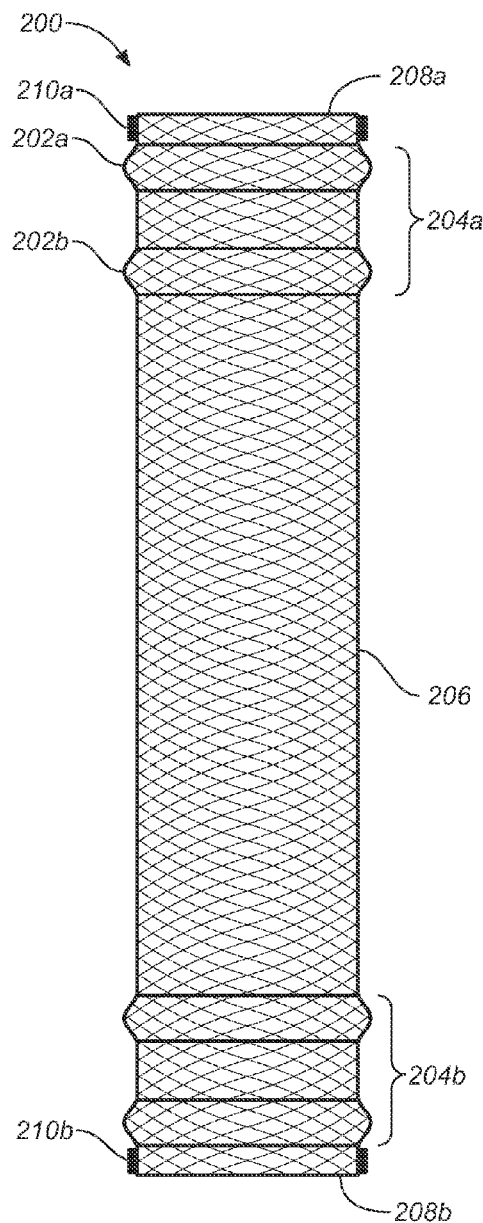
FIG. 2 is a front view of a braided, generally tubular embodiment according to the invention.

Prosthesis 100 can be constructed as a stent (e.g., a tubular wire support structure with graft material at its end portions to form the channel with the raised portions), graft (e.g., a tubular member comprising graft material), or stent-graft (e.g., a stent having an inner and/or outer covering comprising a layer of graft material and which may be referred to as a covered stent), and therefore can be a braided tubular member as is shown for exemplary purposes in FIG. 2 and generally designated with reference numeral 200.

Referring to FIG. 2, exemplary tubular braided prosthesis 200, which is a self-expanding prosthesis, is shown with the same configuration as prosthesis 100 and further includes radiopaque markers 210a and 210b, which can be secured to the prosthesis with, for example sutures. That is, the raised portions 202a, b, sealing portion 204a, b, central portion 206 and end portions 208a, b, have the same configuration as the elements indicated with corresponding 100 series numerals and form similar channels and chambers. The braid can be a metallic braid (e.g., nitinol, stainless steel, or elgiloy braid), polyester (e.g., polyethylene or polyurethane braid), or a combination of both metallic and polymeric materials. The braid can be heat set, crimped, or otherwise configured to integrally form the radially outward extending raised portions on the exterior of the device. For example, a braided nitinol tubular member can be either plastically deformed to maintain the memory shape shown in FIG. 2 or heat treated to acquire such memory shape with conventional methods. In this manner, the prosthesis has a one-piece or unitary construction as the raised portions are integrally formed therewith. The braided construction enables the raised portions to have a minimal effect if any on the delivery profile as the braid is longitudinally stretched when it is radially compressed for delivery.

Figure 3:
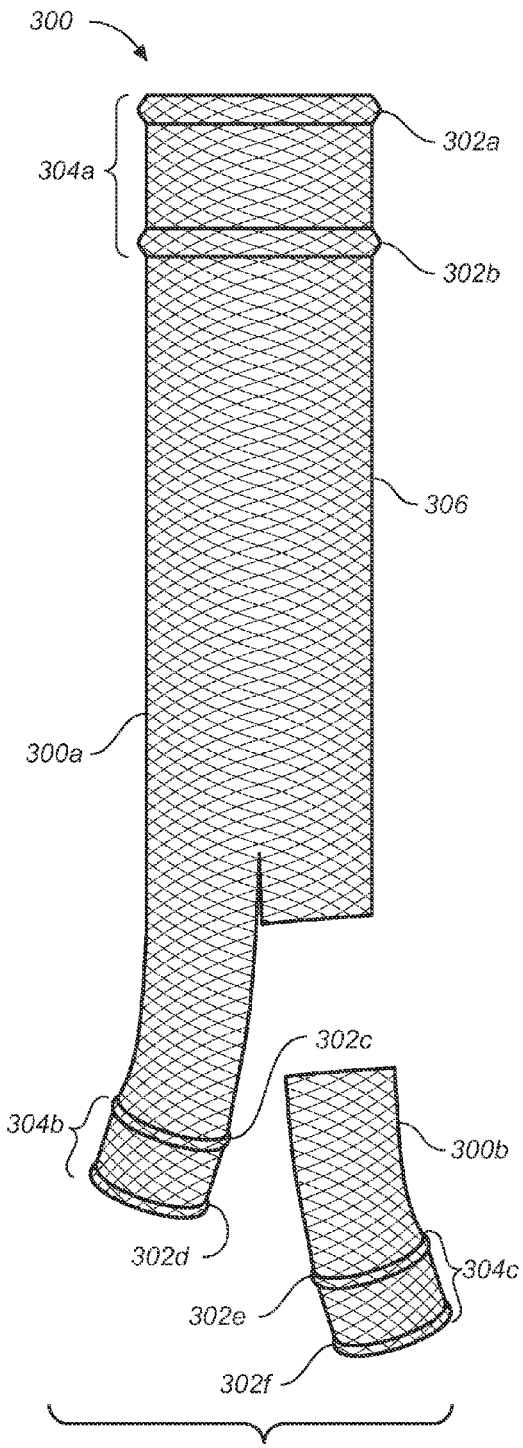
FIG. 3 is a front view of a modular bifurcated embodiment according to the invention.

Referring to FIG. 3, another embodiment of the prosthesis is shown and generally designated with reference numeral 300. Prosthesis 300 is generally the same as prosthesis 200 with the exception that it is bifurcated and is shown without portions corresponding to end portions 208a, b. Prosthesis 300 comprises braided material and raised portions 302a, b, c, d, e, f, and can be formed in the same manner as raised portions 202 to form sealing portions 304a, b, c. Each raised portion pair similarly forms a channel with the portion of the prosthesis therebetween. Prosthesis 300 includes central portion 306, which extends between the raised portion pairs. Prosthesis 300 also has a modular construction, which includes portions 300a and 300b to facilitate delivery and deployment at a bifurcated passageway such as where the aorta branches to the iliac arteries. The contralateral leg 300b can be coupled to main portion 300a in situ as is known in the art. It should be understood that the raised portions need not be provided at each sealing location as described above. For example, the raised portions at either or both of the ipsilateral and contralateral legs at the distal end of the device may be omitted.

Referring to FIG. 4, another embodiment is shown and generally designated with reference numeral 400. In this embodiment, inflatable rings 402a, b, c, d (shown only in cross section) are incorporated on the exterior of the device to form the raised portions. Prosthesis or stent-graft 400 comprises undulating wire spring elements 401a, b, c, d, e, which are shown as might be seen in an X-ray image view in the FIG. 4, and graft portion 403, which can be positioned on the interior and/or exterior of the wire spring elements 401a, b, c, d, e, which can be secured thereto with conventional means such as sutures. Support springs 412a, b can be provided at one or as shown on both ends to provide radial strength and also can be positioned on the interior and/or exterior of graft portion 400b and similarly secured thereto with conventional means. Bare springs 414a, b, described above and shown with an undulating configuration, also can be attached with such conventional means to the ends of graft portion 403 to enhance fixation. Support springs 412a, b, which in this embodiment are shown as undulating wire elements, and undulating bare springs 414a, b also are shown in an X-ray image view. The spring elements, support springs and bare springs can be of any suitable material as would be apparent to one of ordinary skill in the art. One suitable material is nitinol. The graft material also can be any suitable material, one of which is polyethylene (Dacron) or expanded polytetrafluoroethylene (ePTFE). Prosthesis 400 further comprises sealing portions 404a, b, central portions, 406, and end portions 408a, b, which are similar to the corresponding elements in prostheses, 100 and 200. And as described above, the raised portions can be provided at both or one end only. Radiopaque rings or ring segments 410a, b also can be provided and secured to the prosthesis with sutures.

Each ring or raised portion comprises an inflatable tubular member (see e.g., 402c1) which forms a lumen (see e.g., 402c2). Rings or raised portions 402a, b, c, d can be made from thin polymer films used to make catheter balloons where the films form the inflatable tubular members. These materials are designed to minimize profile for endovascular use. The rings or raised portions 402a, b, c, d can be inflated with a medium comprising one or more of a solid, fluid, gel or other suitable substance or material using detachable catheters. Each catheter is fluidly coupled to one of the inflatable rings, delivered with the tubular prosthesis, and removed after the rings have been inflated. Ring deflation can be minimized or avoided by having the connecting site seal after removal of the catheters as is known in the art. For example, the inflation medium can be introduced through an injection port that is coupled to an inflatable ring. The injection port can comprise a small tubular member and a one-way or sealing valve incorporated therein and so arranged that fluid can be delivered through the one-way or sealing valve and into the ring. Alternatively, an inflation medium that maintains structural integrity of the ring without a fluid tight seal can be used. For example, the medium can be a fluid having a viscosity such that the fluid does not exit the opening in the ring through which it was injected. The fluid also can be selected to form a seal as is known in the art. In a further alternative, the medium can comprise a fluid that sets into a solid state and does not require any injection passage to be sealed. One such medium would be an epoxy. In yet a further alternative, when a quick setting substance is injected between adjacent rings 402a, b or 402c, d, a fluid such as air or carbon dioxide can be used to fill the rings and allowed to escape after the substance in the chamber has set. In another variation, the inflation medium also can contain a contrast medium to assist with imaging during positioning and deployment as an alternative to radiopaque markers 410a, b. Contrast mediums including radiopaque materials are known. One such material can contain, for example, iodine, which can be in particulate, liquid, powder or other suitable form.

Figure 4A:
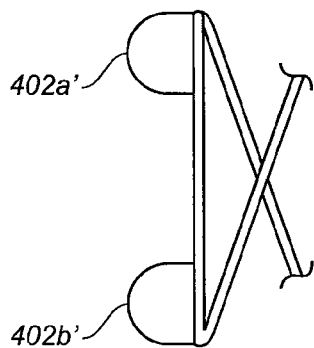
FIG. 4A is a sectional view of an alternate raised portion according to the embodiment illustrated in FIG. 4.
Figure 4:
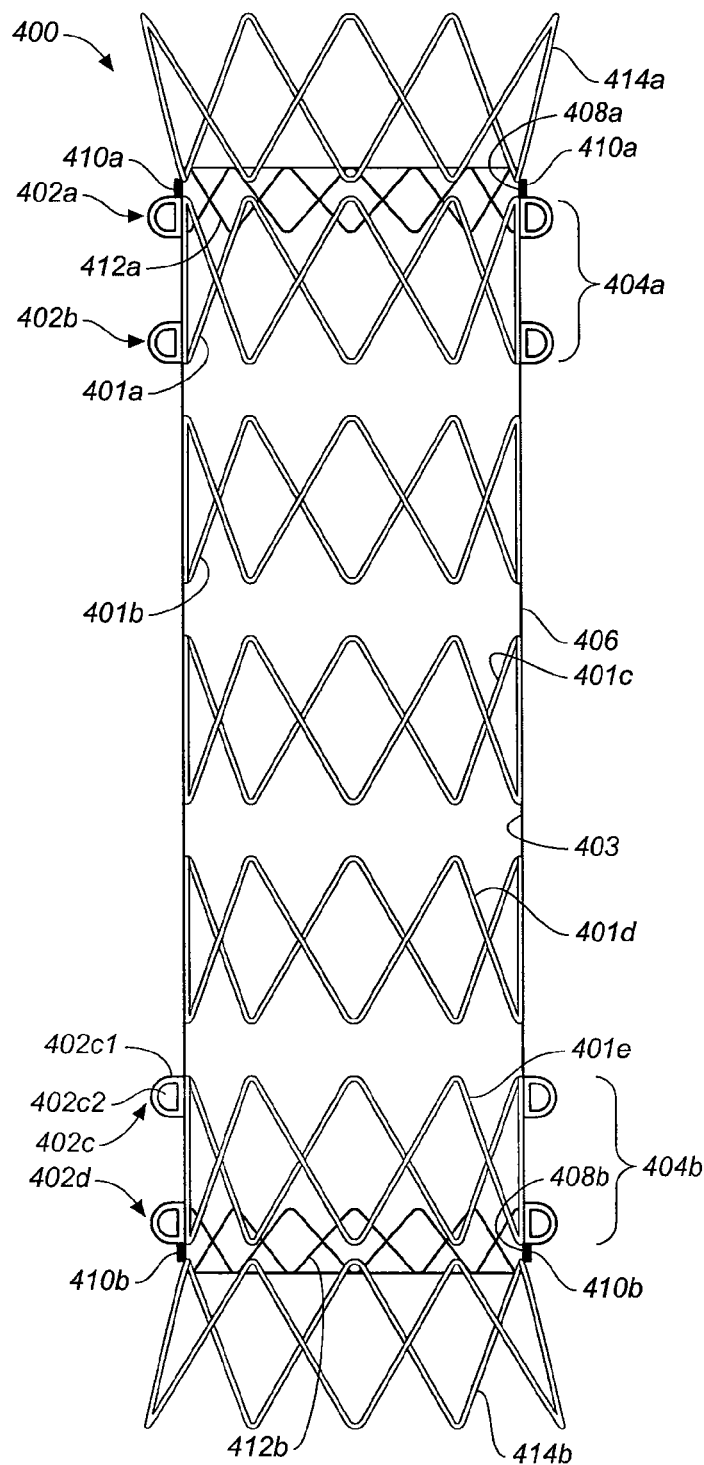
FIG. 4 is a partial schematicized sectional view of another embodiment according to the invention.

Referring to FIG. 4A, a variation of the rings or raised portions 402a, b, c, d is shown and designated with reference numeral 402a' and 402b'. Rings 402a' and 402b' are foam cuffs that are attached to the exterior of the device. The foam is highly compressible, thus minimizing any increase in delivery profile. One exemplary suitable foam material is polyurethane. Rings 402a, b, c, d or 402a' and 402b' can be secured to the device with any suitable biocompatible adhesive such as a cyanoacrylate or they can be secured with sutures or any other suitable means. Further, inflatable ring or raised portions 402a, b, c, d or foam ring or raised portions 402a' and 402b', can be used in place of any of the other raised portions described herein or shown in the drawings.

Figure 5:
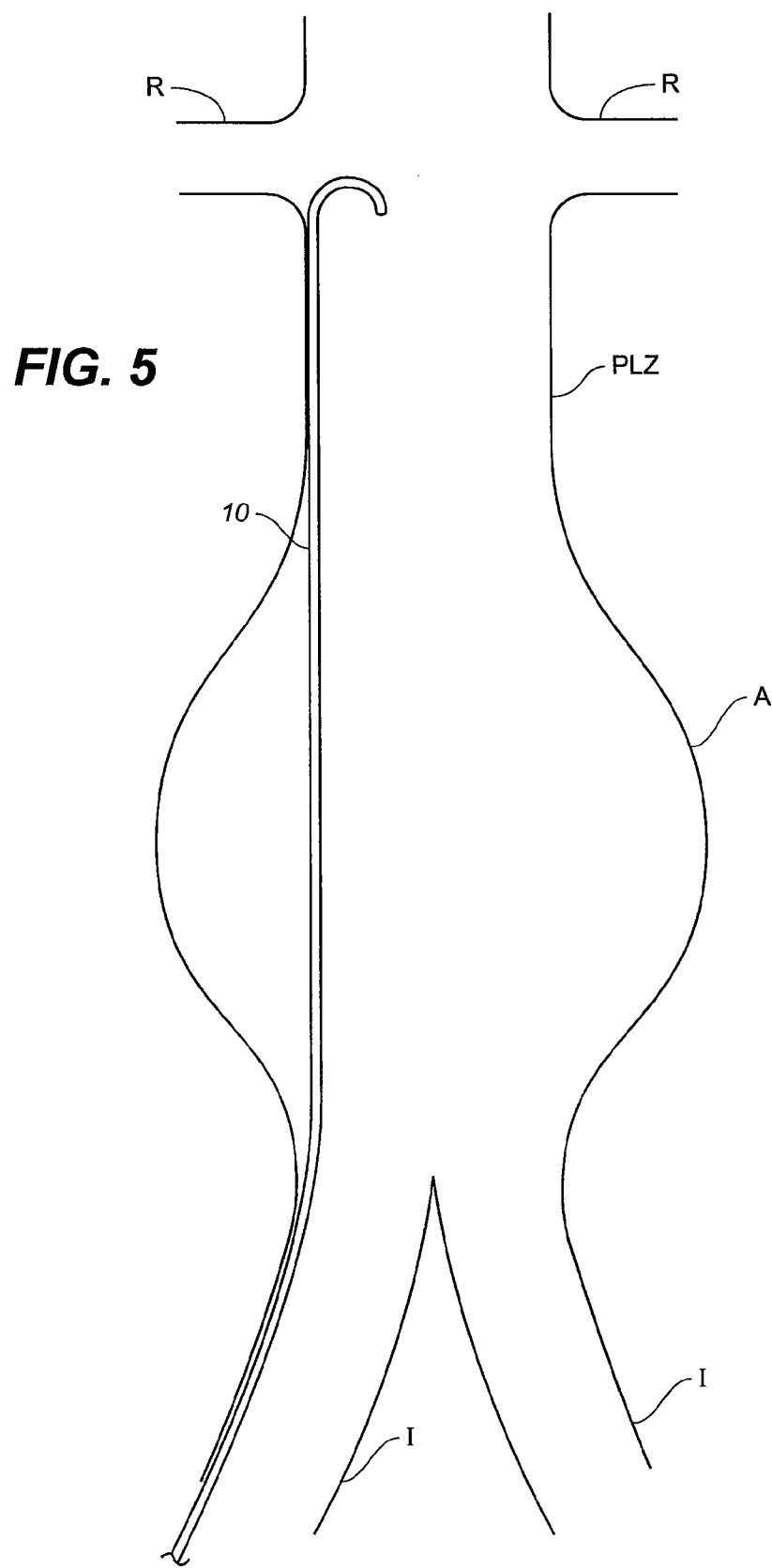
FIGS. 5-8 are diagrammatic views illustrating one method of using the endoluminal device of FIG. 3 and variations thereof, where

FIGS. 5-8 are diagrammatic views illustrating one exemplary method of using endoluminal device 300. FIG. 5 depicts a portion of the aorta between renal arteries "R" and iliac arteries "I" where an abdominal aortic aneurysm "A" is to be treated. The portion of the aorta between the aneurysm "A" and the renal arteries "R" is referred to herein as the neck or landing zone, which is the portion of the aorta to which the proximal portion of the graft will be secured.

Prior to positioning the prosthesis or bifurcated graft at the target location, a contrast delivery catheter such as catheter 10 can be positioned with its pigtail discharge or outlet end in the vicinity of the renal arteries (FIG. 5). Contrast can then be injected into the area to assist in imaging the relative positions of the renal arteries and the prosthesis as is known in the art. A conventional stent graft delivery catheter can be used to deliver the stent graft to the target site through, for example, the femoral arteries as is known in the art. The stent graft, which is a self-expanding stent graft, is compressed and held compressed by use of a sheath and tracked over a guide wire to the delivery location. The stent graft can be deployed by sheath retraction at the target site with conventional means.

Figure 6:
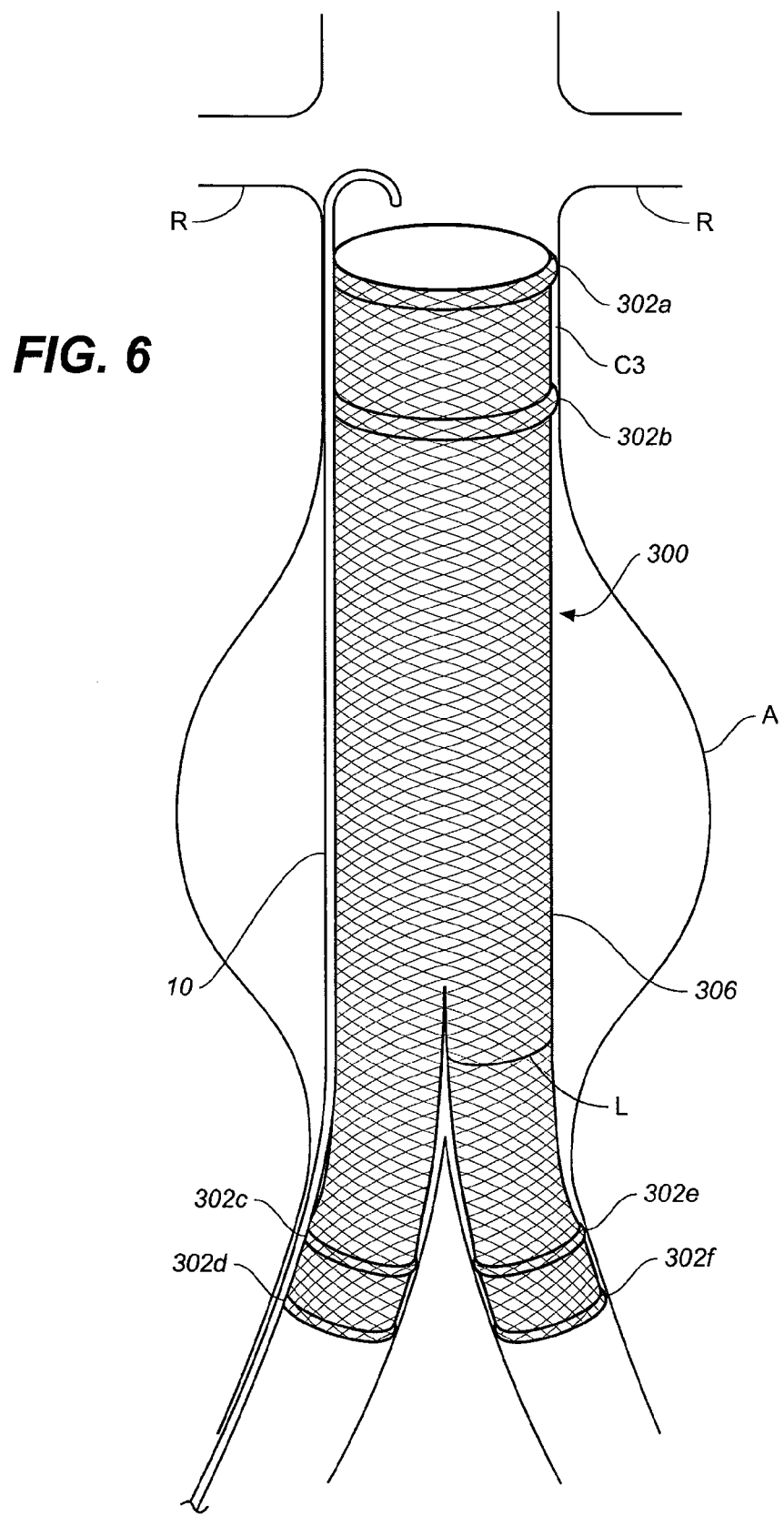

Section 300a can be endoluminally delivered through one of the iliac arteries and deployed and then section 300b can be endoluminally delivered with a separate delivery catheter through the other iliac artery and connected to section 300a as is known in the art. FIG. 6 illustrates bifurcated graft 300 fully deployed and positioned to bypass the aneurysm. Raised portions 302a, b, which are positioned in the proximal neck of the aorta, and the portion of the prosthesis between these raised portions form a 360° annular channel, which with the inner wall of the proximal neck of the aorta, form a 360° annular chamber "C3" into which the selected substance will be placed. The ipsilateral and contralateral leg raised portions 302c, d and 302e, f and the prosthesis portions therebetween also form chambers with the inner walls of the iliac arteries into which the selected substance can be placed.

Figure 7:
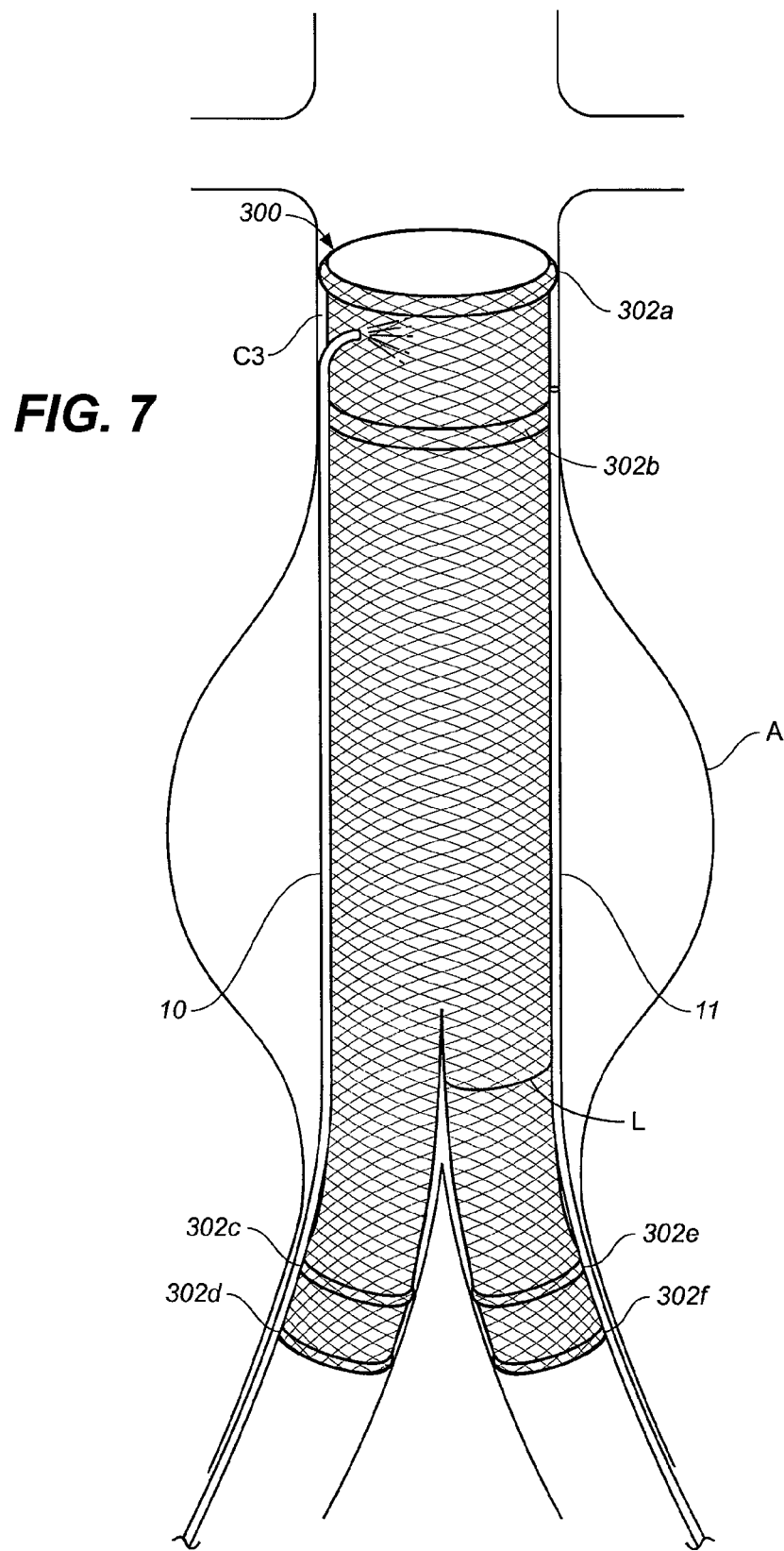

Referring to FIG. 7, contrast delivery catheter 10 is partially withdrawn so that its outlet is positioned in the proximal neck between raised portions 302a, b. The selected substance (e.g., a cocktail of any one or combination of the active substances described above) is delivered through catheter 10 and injected into chamber "C3" to fill or substantially fill the chamber. An optional fluid discharge or evacuation tube or catheter 11 can be positioned with its outlet or distal end in chamber "C3" before or after contrast delivery tube 10 is positioned with its outlet positioned in the same chamber to facilitate fluid (e.g., blood) discharge or evacuation from the chamber before or during delivery of the substance through delivery catheter 10. Discharge or evacuation tube or catheter 11 avoids undesirable chamber pressure build up when filling the chamber with the selected substance. The delivery and evacuation tubes or catheters can be spaced less than 180° from one another or at about 180° from each other as shown. The farther they are spaced from one another, the less likely delivery substance will be discharged through the evacuation tube. The proximal end of evacuation tube or catheter 11 is positioned outside the patient and can be coupled to a conventional vacuum device so that fluid from the chamber can be controllably extracted. A contrast medium such as described above can be delivered with the delivery substance to chamber "C3" and the chamber fluoroscopically monitored to determine when it is filled or substantially filled with the substance. Alternatively, evacuation tube 11 can be fluoroscopically monitored to detect when the selected delivery substance and contrast medium enters tube 11. And in a further alternative, one can detect when the selected delivery substance exits tube 11 outside the patient so that contrast medium need not be used.

Another fluid evacuation tube or catheter (not shown) can be provided to drain or extract fluid form the ipsilateral leg chamber formed between raised portions 302c and 302d. A contrast medium also can be delivered with the delivery substance to the ipsilateral leg chamber and the chamber fluoroscopically monitored in the same manner described above.

Figure 7B:
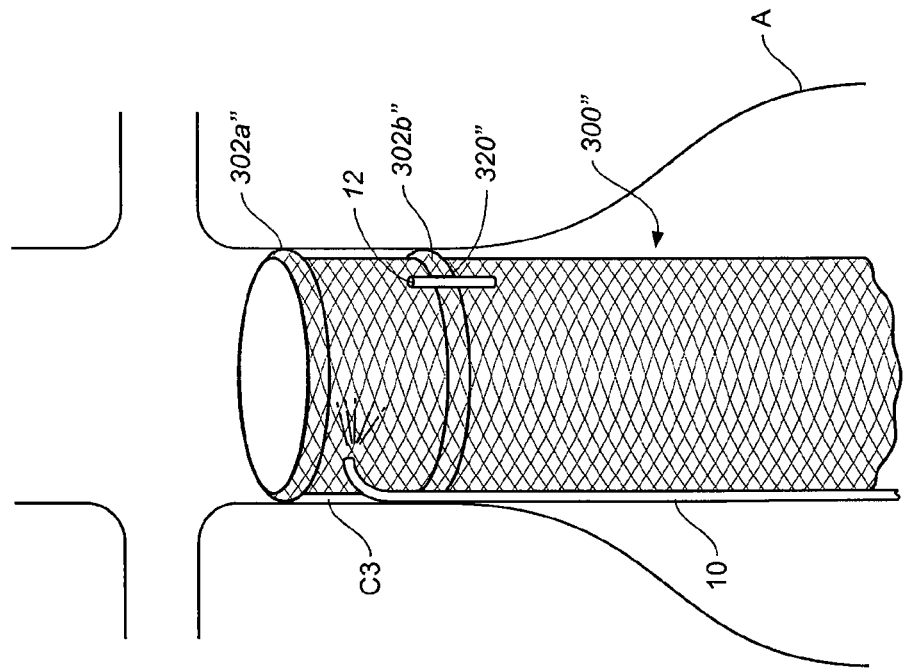
FIGS. 7A and 7B illustrate alternative fluid discharge or evacuation mechanisms.
Figure 7A:
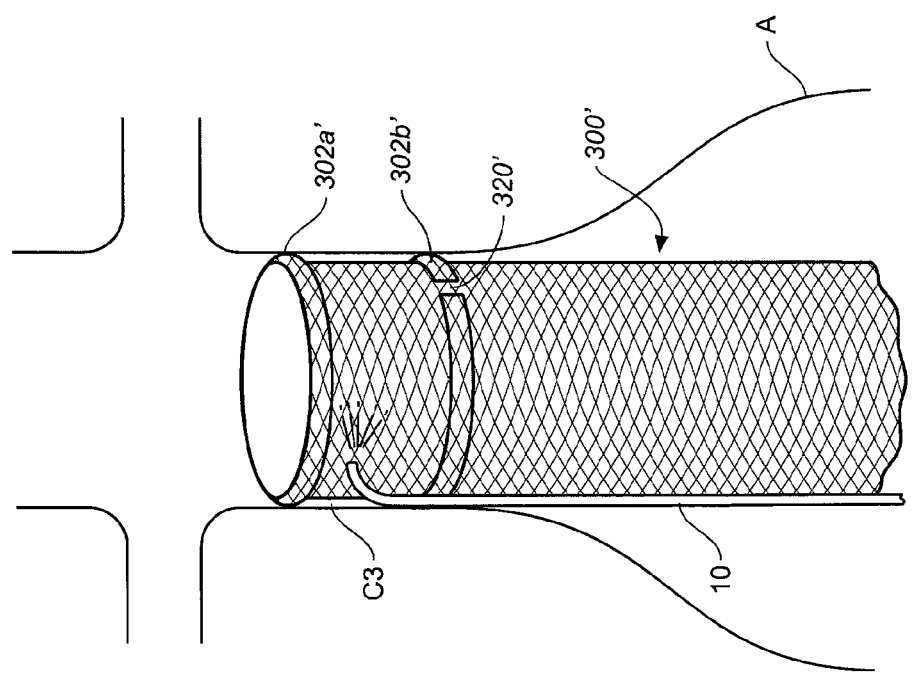

Referring to FIGS 7A and 7B, alternative endoluminal device embodiments to that shown in FIG. 3 with alternative optional fluid discharge or evacuation mechanisms are illustrated and designated with reference numerals 300' and 300".

Endoluminal device 300' includes separate raised portions 302a' and 302b' arranged in a similar manner as compared to raised portions 302a and 302b. Raised portion or annular ring 302a' similarly extends 360°, but raised portion 302b' extends less than 360° such that a relatively small gap or space 320' between the ends of the raised portion is formed. Gap or space 320' extends in a circumferential direction about 3 to 10 degrees and provides a discharge outlet or port to allow fluid discharge from chamber "C3." The gaps can be spaced less than 180° from delivery tube 10 as shown or at about 180° from delivery tube 10. The farther they are spaced from the delivery tube, the less likely delivery substance will be discharged therethrough. A similar gap can be provided in the ipsilateral and contralateral distal raised portions corresponding to raised portions 302d and 302f in device 300.

Endoluminal device 300" also includes separate annular raised portions 302a" and 302b" which have the same configuration and arrangement as raised portions 302a' and 302b'. Raised portion or annular ring 302a" similarly extends 360°, but raised portion 302b" extends less than 360° such that a relatively small gap or space 320", which can have the same size and configuration as gap or space 320', is formed. In this embodiment, a discharge or evacuation tube 12 is positioned in gap 320" to facilitate fluid discharge from the chamber and fixedly secured to the prosthesis with biomedical adhesive or other suitable means. Tube 12 typically has a length of about 5 to 10 mm. The gaps and tubes can be spaced less than 180° from delivery tube 10 as shown or at about 180° from delivery tube 10. The farther they are spaced from the delivery tube, the less likely delivery substance will be discharged therethrough. A similar gap and tube can be provided in ipsilateral and contralateral distal raised portions corresponding to raised portions 302d and 302f in device 300. Alternatively, removable tubers having the same construction as tube 11 can be used to drain fluid form the ipsilateral and contralateral chambers.

Figure 7C:
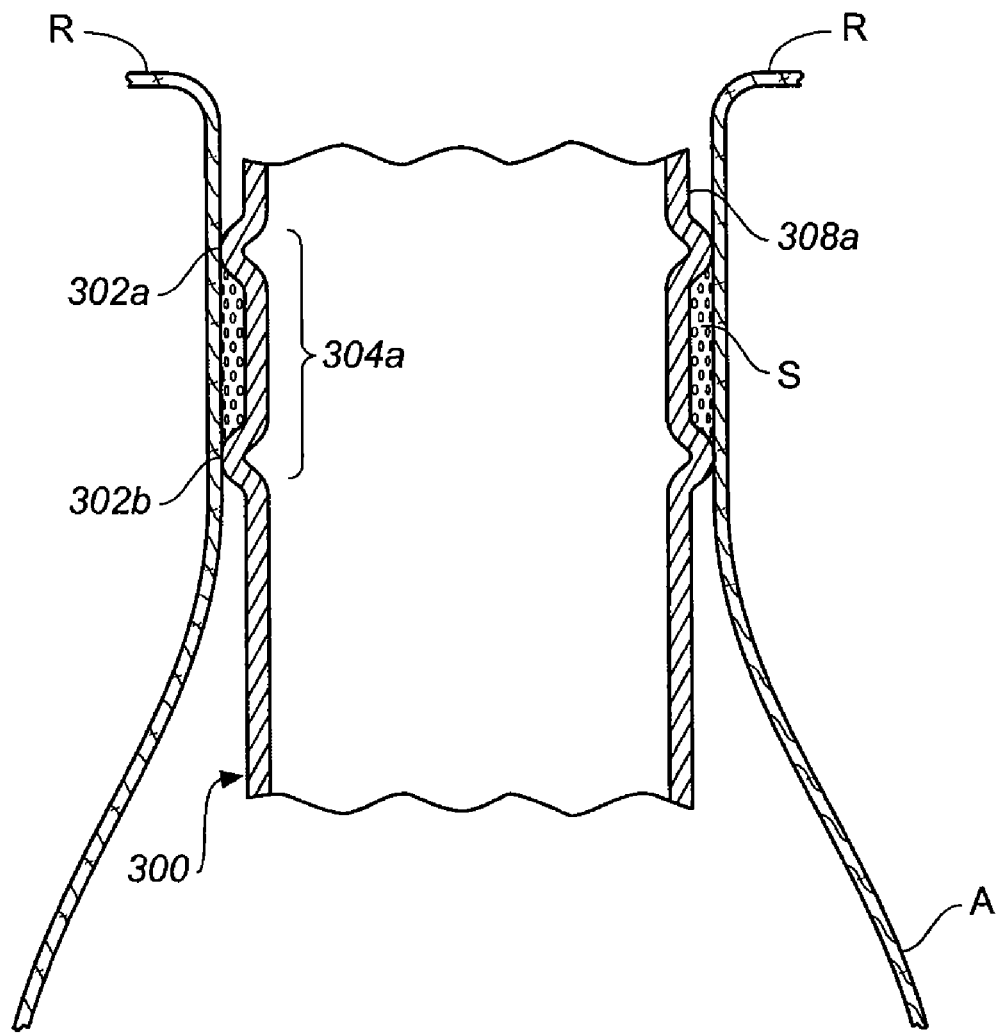
FIG. 7C is an enlarged view of the proximal neck showing the substance that was introduced between the raised portions.

FIG. 7C is an enlarged view of the proximal neck showing the chamber of FIG. 7 filled with the substance, which is designated with reference character "S." The prosthesis and contained substance can block fluid flow and minimize or eliminate the risk of incursion of fluid into the aneurysm. When the substance is an adhesive, the adhesive firmly anchors the prosthesis at the target location.

Catheter 10 is then further withdrawn until its outlet is positioned in the ipsilateral leg chamber where additional amounts of the substance are injected to fill that chamber after which the catheter can be fully withdrawn. Any of the foregoing fluid discharge or evacuation mechanisms can be used to drain chamber fluid as described above. For example, a catheter having the same construction as catheter 11 can be positioned with its inlet between raised portions 302c and 302d and used in the same manner.

It should be understood that other substance delivery and fluid discharge or evacuation catheter or tube arrangements can be used such as any of the other delivery tubes or catheter systems described herein or combinations thereof.

Figure 8:
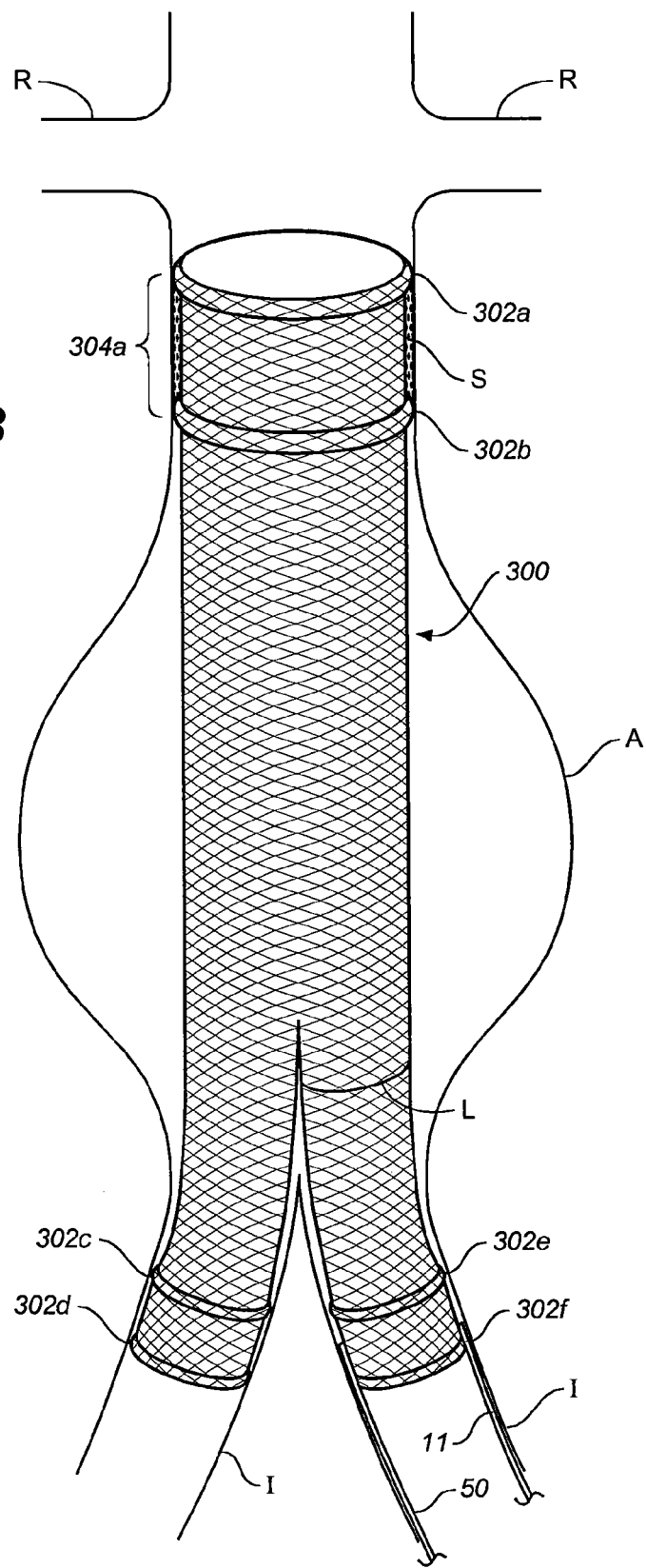

The contralateral chamber is then filled. When discharge or evacuation tube or catheter 11 is used, it is partially withdrawn so that its outlet is positioned in the contralateral chamber between raised portions 302e and 302f for extracting fluid therefrom as described above. A separate fill catheter is provided with or after the delivery of the contralateral leg to deliver the active substance to the contralateral chamber. One such catheter is diagrammatically illustrated in FIG. 8 and designated with reference numeral 50. Referring to FIG. 8, catheters 11 and 50 are shown being withdrawn after the chamber has been filled. Alternatively, other suitable means for delivering the substance to and discharging fluid from the contralateral leg chamber can be used including any of the tubes or catheter systems described herein or combinations thereof Further, the contralateral leg my not be delivered and secured in position until the section 300a is delivered and its chambers filled with the active substance.

Referring to FIGS. 9, 10A-E, and 11A and B, other substance delivery and evacuation tube or catheter configurations are shown where the substance delivery and evacuation tubes can be releasably attached to the prosthesis and delivered therewith. The substance delivery and evacuation tubes typically are about 20-45 cm long when used in abdominal aortic aneurysm applications. Tubes 10 and 11 also typically have this length for this application.

Referring to FIG. 9, a delivery tube 20 can be releasably secured with sutures 22 to prosthesis 300 so that its outlet port is positioned in the prosthesis channel between raised portions. The sutures can be severed and the tube withdrawn after the substance has been delivered. Another tube having the same construction as tube 20 can be releasably secured to the prosthesis in the same manner to function as a discharge tube and drain the chamber formed between raised portions 302a, b and the inner wall of the lumen being treated. It can be spaced less than or at about 180 from tube 20 as described above in connection with other discharge tubes. Further, any of the foregoing prosthesis embodiments can incorporate such a delivery or discharge tube to prosthesis connection.

In the embodiments shown in FIGS. 10A-B, delivery tube or catheter system 30a and optional discharge or evacuation catheter system 30b are shown. Delivery tube system 30a comprises tubes 32a and 34a discharge system 30b comprises tubes 32b and 34b. Tubes 32a, b are secured to the prosthesis, with any suitable means such as sutures or biocompatible adhesive, and their outlet ports positioned in the prosthesis channel between the raised portions. Each tube 34a, b has one end releasably coupled or slidably disposed in a respective tube 32a, b so that it can be removed after the procedure. The other or remote ends of tubes 32a, b (not shown) are outside the patient. The embodiment of FIGS. 10A and B have tubes 32*a*, *b* extending over one of the raised portions in the same manner that tube 20 is shown extending over raised portion 302*b* in FIG. 9.

Figure 10C:
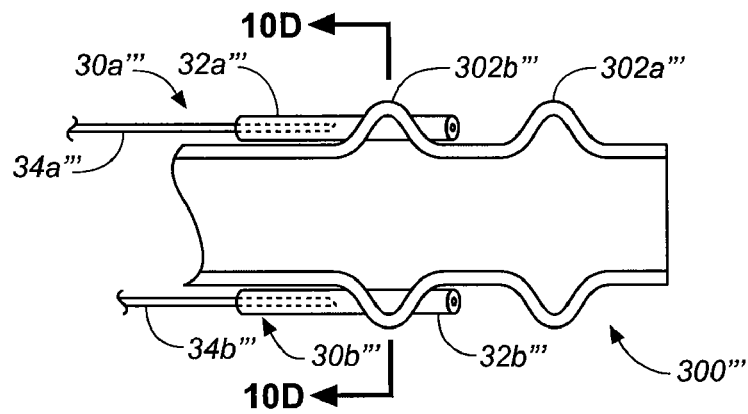
FIG. 10C illustrates a further embodiment where the substance delivery tube or lumen extends through a small opening in one of the raised portions.
Figure 10D:
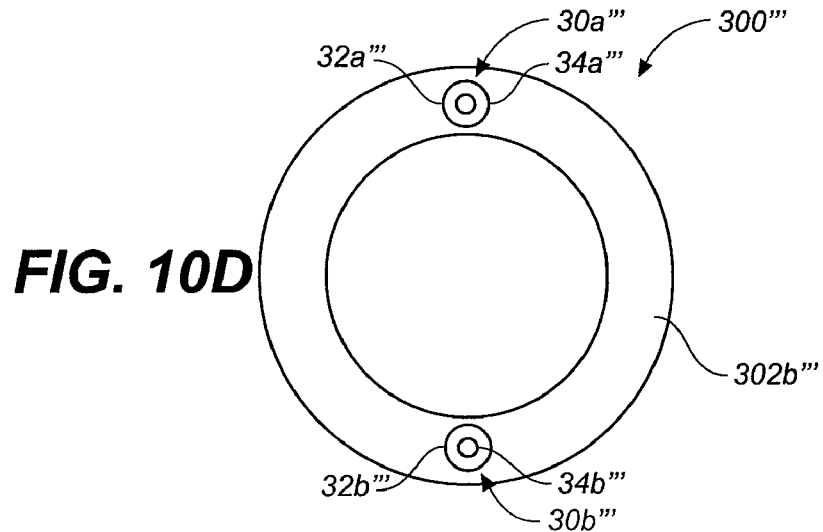
FIG. 10D is a sectional view taken along line 10C-10C in FIG. 10C.

Referring to the embodiment of FIGS. 10C and 10D, delivery and discharge tubes extend through an opening formed in the raised the raised portions and fixedly secured to the prosthesis with sutures, adhesive or other conventional means. When the prosthesis has a braided construction, the braid can be separated at the desired location to form the opening for a respective tube to pass through. In the illustrative embodiment, prosthesis 300′″ has annular raised portions 302*a*′″ and 302*b*′″, which correspond to raised portions 302*a* and 302*b* in size and configuration and extend in a circumferential direction 360°. Each delivery tube system 30*a*′″ and 30*b*′″ comprises a respective tube 32*a*′″ and 32*b*′″, which extends through the aforementioned openings in raised portion 302*a*′″ (see e.g., FIG. 10D), and tubes 34*a*′″ and 34*b*′″, which are releasably coupled to or slidably disposed in tubes 32*a*′″ and 32*b*′″. In this manner tubes 34*a*′″ and 34*b*′″ can be withdrawn after the procedure. Tubes 32*a*′″ and 32*b*′″ can be arranged 180° degrees from one another as shown or as described above.

Figure 10E:
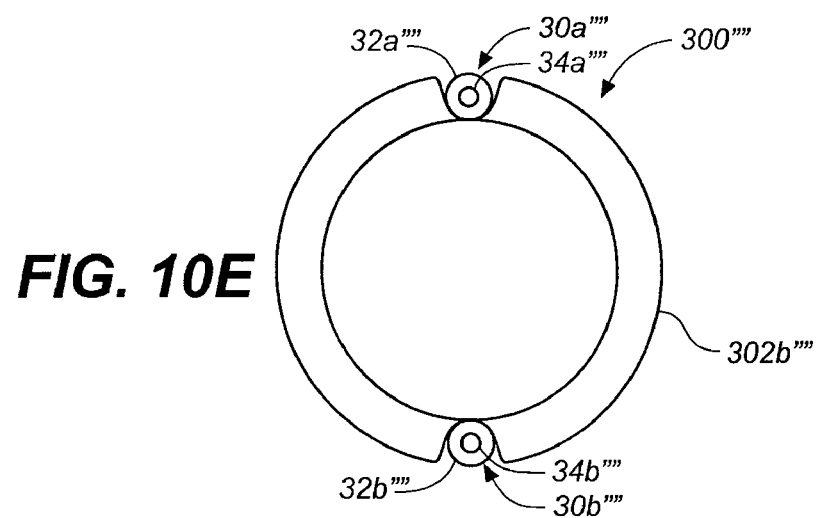
FIG. 10E is a sectional view of another embodiment where one raised portion has a gap into which the substance delivery and fluid discharge or evacuation tubes are placed.

Referring to FIG. 10E, a variation of the embodiment shown in FIGS. 10C and 10D is shown and designated with reference numeral 300″″. Prosthesis 300″″ is the same as prosthesis 300′″ with the exception that the inner raised portion 302*b*″″ has two recesses, each sized to receive one of delivery tube systems 30*a*″″ and 30*b*″″. Each delivery tube system 30*a*″″ and 30*b*″″ comprises a respective tube 32*a*″″ and 32*b*″″, which is fixedly secured in one of the recesses, and tubes 34*a*″″ and 34*b*″″, which are releasably coupled to or slidably disposed in tubes 32*a*″″ and 32*b*″″. In this manner tubes 34*a*″″ and 34*b*″″ can be withdrawn after the procedure. Tubes 32*a*″″ and 32*b*″″ can be arranged 180° degrees from one another as shown or as described above.

Figure 11B:
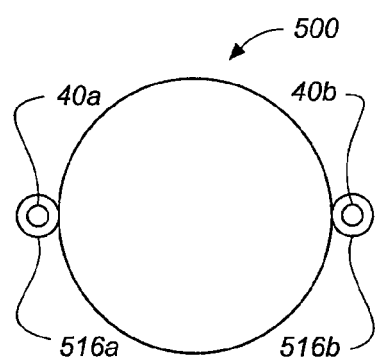
FIG. 11B is a sectional view of the endoluminal device, tubular member and delivery tube of FIG. 11A taken along line 11B-11B.

Referring to FIGS. 11A and 11B, further alternative delivery and discharge tube arrangements or systems are shown as well as an alternative multiple channel prosthesis configuration. In the illustrative embodiment where exemplary prosthesis is generally indicated with reference numeral 500, tubular member 516*a* and optional tubular member 516*b* form a support and/or guide for substance delivery tube or catheter 40*a* and optional discharge or evacuation tube or catheter 40*b*. Tubular members 516*a*, *b* are sized to completely fit within the aneurysmal sac and not extend therebeyond or into any of the aneurysmal necks. They can be circumferentially arranged in the same manner as any of the delivery and discharge tube arrangements described above. They also are fixedly secured to prosthesis 500 with sutures, adhesive or other suitable means or they are integrally formed with the prosthesis. Therefore, tubular members 516*a*, *b* and the remainder of prosthesis can, for example, be integrally formed from braid such as metallic braid as a one piece construction. The outlet of tubes 40*a*, *b* can be positioned between the outermost raised portions prior to delivery of the prosthesis. In this manner, tube 40*a* is ready to deliver the selected substance between the raised portions and tube 40*b* is ready to drain the chamber formed between the raised portions upon delivery and deployment of the prosthesis.

Either or both of these substance delivery and chamber discharge tube arrangements or systems also can be used as an alternative to any of the substance delivery and chamber discharge arrangements described above.

The embodiment of FIGS. 11A and 11B also depict an exemplary multiple channel configuration where more than two raised portions or rings are provided in a single neck region of the prosthesis. Such multiple channel configurations also can be incorporated into any of the embodiments described above. This construction can be used to improve performance by providing redundancy of containment. It also can be used to provide the prosthesis with the ability to accommodate aneurysmal necks of significantly different lengths, thereby tailoring the treatment to the length of the neck with a single device.

Referring to FIG. 11A, prosthesis 500 is shown with the same construction as prosthesis 300 with the exception that prosthesis 500 has four 360° annular raised portions 502 in the proximal neck that form three channels, the annular width of sealing portions 504 in the proximal neck is reduced as compared sealing portions 304, and tubular members 516*a*, *b* is fixedly attached to the outside of central portion 506 of the prosthesis or integrally formed therewith. Although three channels are shown, it should be understood that any suitable number of channels can be used in the multiple channel arrangement. Accordingly, there can be three or more raised portions or two or more channels.

In use, prosthesis 500 is deployed and the active substance injected into the outermost chamber between raised portions 502*a* and 502*b*. Chamber fluid can be drained or evacuated via tube 40*b*, which also has its distal end between raised portions 502*a* and 502*b*. Then tubes 40*a* and 40*b* are partially withdrawn so that their distal ends are positioned in the middle chamber between the middle two raised portions 502*b* and 502*c*. In this position active substance is delivered and chamber fluid drained. Since the inner one of these raised portions, raised portion 502*c*, is at the juncture of the neck and beginning of the aneurysmal sac, tubes 40*a* and 40*b* are withdrawn past the next channel in the proximal neck of the device and positioned in the ipsilateral leg and contralateral leg chambers as described above. Although the third channel from the proximal end extends into the aneurysm and is not used to contain the substance, it provides the ability to accommodate longer aortic proximal necks when such are encountered. Substance delivery tube or catheter 50 can be provided for the contralateral leg chamber and discharge tube or tube or catheter 11 can be provided for the ipsilateral leg chamber as shown in FIG. 11A and as described above.

Although prosthesis 500 is shown with more than two raised portions at the proximal neck, it should be understood that this neck configuration where the raised portions form multiple 360° annular channels, can be incorporated into either one or both of the distal necks of the device, which extend into the iliac arteries. Furthermore, any one or combination of the necks may not include any raised portions depending on the application. In addition, any of the substance delivery mechanisms described above can replace any combination of tubular members 516*a*, *b* and substance delivery and discharge catheter 40*a*, *b*. Further, the multiple channel configuration in a single neck region of the prosthesis as depicted in FIG. 11A can be incorporated into any number of the necks of any of the prostheses described herein.

Any feature described in any one embodiment described herein can be combined with any other feature of any of the other embodiments whether preferred or not.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto.

What is claimed is:

1. A tubular prosthesis comprising a non-inflatable tubular member adapted for placement in a lumen in a human body where the lumen has a wall, said tubular member having first and second ends, first and second raised portions that are separate from one another and adjacent to one of said ends, and an intermediate portion between said raised portions, which together with said raised portions forms a channel, each raised portion extending in a circumferential direction about said tubular member, being integrally formed in said tubular member, and configured to form with said wall a chamber in which a substance that can enhance sealing or fixation or provide therapeutic benefit can be placed, wherein said channel has a width of about 2-30 mm and wherein each raised portion extends about 1-5 mm radially outward from an area adjacent to said intermediate portion.

2. The prosthesis of claim 1 wherein said tubular member comprises crimped portions and said crimped portions form said raised portions.

3. The prosthesis of claim 2 wherein said tubular member comprises braided material.

4. The prosthesis of claim 3 wherein said braided material comprises metallic material.

5. The prosthesis of claim 3 wherein said braided material comprises metallic and polymeric material.

6. The prosthesis of claim 1 wherein said tubular member comprises third and fourth raised portions adjacent to the other one of said end portions, each of said third and fourth raised portions being annular and integrally formed in said tubular member.

7. The prosthesis of claim 1 wherein said tubular member comprises a third raised portion, said second and third raised portions forming a channel therebetween.

8. The prosthesis of claim 1 wherein said tubular member is bifurcated.

9. The prosthesis of claim 1 wherein said prosthesis is a vascular stent graft.

10. The prosthesis of claim 1 wherein said channel has a width of about 2-10 mm.

11. The prosthesis of claim 1 wherein said raised portions have a base width of about 2 mm.

12. A tubular prosthesis comprising a tubular member adapted for placement in a lumen in a human body where the lumen has a wall, said tubular member having first and second end portions, first and second raised portions adjacent to one of said end portions, and an intermediate portion between said raised portions, which together with said raised portions forms a channel, each raised portion being annular and integrally formed in said tubular member and said tubular member comprising braided material, said raised portions being configured to form with said wall a chamber in which a substance that can enhance sealing or fixation or provide therapeutic benefit can be placed, wherein said channel has a width of about 2-30 mm and wherein each raised portion extends about 1-5 mm radially outward from an area adjacent to said intermediate portion and has a base width of about 2 mm.

13. The prosthesis of claim 12 wherein said channel has a width of about 2-10 mm.

14. A tubular prosthesis system comprising:
a tubular member adapted for placement in a passageway having a wall and being in a human body, said tubular member having first and second end portions, first and second raised portions that are separate from one another, each extending in a circumferential direction about said tubular member, and an intermediate portion between said raised portions, which together with said raised portions forms a channel, and said raised portions being exposed so that said raised portions can directly engage said wall to form a chamber into which a substance can be delivered when the tubular prosthesis is positioned at a target location in the passageway; and
a delivery tube secured to said tubular member, said delivery tube having an inlet and an outlet, said outlet being disposed between said raised portions and arranged to deliver a substance therebetween.

15. The system of claim 14 wherein said delivery tube is releasably secured to said tubular member.

16. The system of claim 15 further including an evacuation tube, said evacuation tube having an inlet and an outlet, said inlet being disposed between said raised portions and arranged to evacuate fluid from between said raised portions.

17. The system of claim 15 wherein one of said raised portions forms a space that allows a substance to pass therethrough.

18. The system of claim 17 wherein one of said raised portions is annular and extends 360°.

19. The system of claim 14 wherein said raised portions are annular and extend 360° and said channel is a 360° annular channel.

20. The system of claim 16 wherein said channel has a width of about 5-30 mm.

21. The system of claim 14 wherein each raised portion extends about 1-5 mm radially outward from an area adjacent to said intermediate portion.

22. The system of claim 21 wherein each raised portion has a base from where it extends radially outward and said base has a width of about 2 mm.

23. The system of claim 14 further including third and fourth annular raised portions, and an intermediate portion therebetween, which together with said third and fourth raised portions form a second 360° annular channel, and said third and fourth raised to form a chamber into which a substance can be delivered when the tubular prosthesis is positioned at a target location in the passageway.

24. The system of claim 14 wherein said tubular member comprises a third annular raised portion and an intermediate portion between said second and third raised portions, which together with said second and third raised portions form a second 360° channel, and said third raised portion being exposed so that said second and third raised portions can directly engage said wall to form a chamber into which a substance can be delivered when the tubular prosthesis is positioned at a target location in the passageway.

25. The system of claim 24 wherein said intermediate portions each have a width of about 5-10 mm.

26. The system of claim 24 wherein at least one of said channels has a width of about 2-10 mm.

27. The system of claim 26 wherein each of said channels has a width of about 2-10 mm.

28. The system of claim 14 wherein said tubular member is a stent-graft.

29. The system of claim 14 wherein said tubular member is bifurcated.

30. The system of claim 14 wherein said tubular member comprises a stent graft.

31. A method of delivering a substance between a prosthesis and a passageway wall in a human body comprising:
positioning a tubular endoluminal prosthesis, having an annular channel formed along a circumferential exterior surface thereof, in a passageway, having a wall and being in a human body, so as to form a discrete chamber with the channel and a portion of said wall; and
introducing a substance into said chamber.

32. The method of claim 31 including providing a prosthesis having annular raised portions that form boundaries of said channel.

33. The method of claim 31 wherein an adhesive is introduced into said chamber to secure the prosthesis to said wall portion.

34. The method of claim 33 wherein a tissue based adhesive is introduced into said chamber.

35. The method of claim 31 wherein growth factor is introduced into said chamber.

36. The method of claim 31 wherein a drug is introduced into said chamber to interact with said wall portion.

37. The method of claim 31 including evacuating fluid from said chamber while introducing the substance.

38. The method of claim 37 including evacuating fluid from said chamber comprises evacuating fluid through a tube having an inlet disposed in said chamber.

39. The method of claim 38 including allowing an amount of the substance to flow in the evacuation tube and detect the flow.

40. The method of claim 31 wherein said endoluminal prosthesis comprises a stent graft and said passageway is a vessel.

* * * * *

UNITED STATES PATENT AND TRADEMARK OFFICE
CERTIFICATE OF CORRECTION

PATENT NO.         : 7,481,836 B2
APPLICATION NO.    : 11/278044
DATED              : January 27, 2009
INVENTOR(S)        : Trevor Greenan It is certified that error appears in the above-identified patent and that said Letters Patent is hereby corrected as shown below:

Column 16, line 5,

"39. The method of claim 38 including allowing an amount of the substance to flow in the evacuation tube and detect the flow."

should be changed to -- 39. The method of claim 38 including allowing an amount of the substance to flow in the evacuation tube and detecting the flow. --

Signed and Sealed this

Twenty-fifth Day of August, 2009

David J. Kappos
*Director of the United States Patent and Trademark Office*